United States Patent
Botbol

(10) Patent No.: US 7,481,770 B2
(45) Date of Patent: Jan. 27, 2009

(54) METHOD AND SYSTEM FOR TISSUE DIFFERENTIATION

(75) Inventor: Meir Botbol, Pardes Hana (IL)

(73) Assignee: DeepBreeze Ltd., Industrial Park or Akiva (IL)

( * ) Notice: Subject to any disclaimer, the term of this patent is extended or adjusted under 35 U.S.C. 154(b) by 622 days.

(21) Appl. No.: 10/771,150

(22) Filed: Feb. 4, 2004

(65) Prior Publication Data
US 2005/0182340 A1 Aug. 18, 2005

(51) Int. Cl.
*A61B 5/02* (2006.01)

(52) U.S. Cl. ...................... 600/481; 600/529

(58) Field of Classification Search ................ 600/481, 600/483, 484, 502, 529, 586; 706/15–44; 367/7, 8
See application file for complete search history.

(56) References Cited

U.S. PATENT DOCUMENTS

| | | | |
|---|---|---|---|
| 5,031,154 A * | 7/1991 | Watanabe | 367/8 |
| 6,105,015 A | 8/2000 | Nguyen et al. | |
| 6,139,505 A | 10/2000 | Murphy | |
| 6,463,438 B1 | 10/2002 | Veltri et al. | |
| 6,625,303 B1 * | 9/2003 | Young et al. | 382/132 |
| 6,672,165 B2 * | 1/2004 | Rather et al. | 73/603 |
| 6,887,208 B2 * | 5/2005 | Kushnir et al. | 600/529 |
| 2003/0130588 A1 * | 7/2003 | Kushnir et al. | 600/529 |
| 2003/0139679 A1 | 7/2003 | Kushnir et al. | |
| 2003/0229278 A1 * | 12/2003 | Sinha | 600/407 |

FOREIGN PATENT DOCUMENTS

| | | |
|---|---|---|
| WO | 03/057037 A1 | 7/2003 |
| WO | WO 03/057037 A1 | 7/2003 |

OTHER PUBLICATIONS

Kompis, M., et al., "Acoustic Imaging of the Human Chest" *Chest*, vol. 120, No. 4, pp. 1309-1321, (2001). XP:002237833.
Kompis, M. et al. "Acoustic Imaging of the Human Chest", *Chest*, vol. 120(4) pp. 1309-1321, 2001.

\* cited by examiner

*Primary Examiner*—Charles A. Marmor, II
*Assistant Examiner*—Anita Saidi
(74) *Attorney, Agent, or Firm*—The Nath Law Group; Susanne M. Hopkins; Ari G. Zytcer

(57) ABSTRACT

A system and method for tissue differentiation. In the method, M acoustic signals $s_i(t)$, i=1 to M, are obtained from M locations on a body surface. The N signals are subjected to band pass filtering using N band-pass filters, so as to generate NXM signals $sij(t)$, i=1 to M, j=1 to N. K images $I_1$ to $I_K$, where K≦N, are then generated using the signals $sij(t)$, i=1 to M, j=1 to N. The pixels are divided into a predetermined number L of categories $C_l$, l from 1 to L, using the images $I_1$ to $I_K$. For each category $C_l$, l from 1 to L, and for each pixel $p(x,y)$, A probability $p_l$ of assigning the pixel $p(x,y)$ to the category $C_l$ is determined. An image may then be generated using the probabilities $p_l$.

12 Claims, 3 Drawing Sheets

METHOD AND SYSTEM FOR TISSUE DIFFERENTIATION

FIELD OF THE INVENTION

This invention relates to methods for classifying tissues.

BACKGROUND OF THE INVENTION

It is known to apply a plurality of microphones onto a body surface in order to record body sounds simultaneously at a plurality of locations on the body surface. U.S. Pat. No. 6,139,505, for example, discloses a system in which microphones are placed around a patient's chest and recordings of the microphones are displayed on a screen or printed on paper. Kompis et al. (*Chest* 120(4):2001) discloses a system in which microphones are placed on a patient's chest to record lung sounds that are analyzed to determine the location in the lungs of the source of a sound detected in the recording.

Applicant's copending application Ser. No. 10/338,742 filed on Jan. 9, 2003 and having the publication number US 2003-0139679 discloses a method and system for analyzing body sounds. A plurality of microphones are affixed to an individual's chest or back. The recorded sound signals are analyzed to determine an average acoustic energy at a plurality of locations over the chest. The determined acoustic energies are then used to form an image of the respiratory tract.

A neural network is an algorithm used to classify elements based upon previously input information on the nature of the elements. U.S. Pat. No. 6,109,270 to Mah et al discloses use of a neural network to classify brain tissue as being either normal or abnormal. U.S. Pat. No. 6,463,438 to Veltri et al. discloses use of a neural network to distinguish between normal and cancer cells.

SUMMARY OF THE INVENTION

The present invention provides a method and system for tissue differentiation. M acoustic signals are obtained during a time interval by placing M microphones on a body surface such as an individuals back or chest. The M acoustic signals are each subjected to frequency band filtering by means of N frequency band filters. For each filter, the M outputs from the filter are input to a first image processor. The first image processor generates an image using the M outputs of the filter. The images may be obtained by any method for generating an image from acoustic signals. For example, the images maybe obtained by the method of Kompis et al. (supra). In a preferred embodiment of the invention, an image is generated by the method disclosed in applicant's WO 03/057037. In the method of WO 03/057037, an image is obtained from M signals $P(x_i,t)$ for i=1 to M, (where the signal $P(x_i,t)$ is indicative of pressure waves at the location $x_i$; on the body surface) by determining an average acoustic energy $P(x,t_1,t_2)$ at at least one position x over a time interval from a first time $t_1$ to a second time $t_2$.

The N images are preferably, but not necessarily, transformed by an SVD (singular value decomposition) processor, as explained in detail below. The output of the SVD processor is input to a self-organizing map neural network and to a classifier. The output of the neural network consists of L N-dimensional vectors where L is a predetermined number of categories of interest. The output from the neural network is input to the classifier.

For each pixel p(x,y), the classifier is configured to calculate a probability of assigning the pixel to each of the L categories. One or more images may then be generated by a second image processor based upon the output from the classifier.

Thus, in its first aspect, the invention provides a method for tissue differentiation comprising:
(a) obtaining M acoustic signals $s_i(t)$, i=1 to M, from M locations on a body surface;
(b) for each of N frequency bands, and for each of the signals $s_i(t)$, i from 1 to M, subjecting the signal $s_i(t)$ to band pass filtering using N band-pass filters, so as to generate NXM signals sij(t), i=1 to M, j=1 to N;
(c) generating K images $I_1$ to $I_K$, where K≦N, using the signals sij(t), i=1 to M, j=1 to N;
(d) dividing pixels into a predetermined number L of categories $C_l$, l from 1 to L, using the images $I_1$ to $I_K$; and
(e) for each category $C_l$, l from 1 to L, and for each pixel p(x,y), calculating a probability $p_l$ of assigning the pixel p(x,y) to the category $C_l$.

In its second aspect, the invention provides a system for tissue differentiation comprising:
a. M sound transducers configured to obtain M acoustic signals $s_i(t)$, i=1 to M, from M locations on a body surface;
b. N band pass filters, each band pass filter being configured to receive each of the signals $s_i(t)$, i from 1 to M, so as to generate NXM signals sij(t), i=1 to M, j=1 to N;
c. A first image generator configured to generate K images $I_1$ to $I_K$, where K≦N, using the signals sij(t), i=1 to M, j=1 to N;
d. a neural network configured to divide pixels into a predetermined number L of categories $C_l$, l from 1 to L, using the images $I_1$ to $I_K$; and
e. a classifier configured, for each category $C_l$, l from 1 to L, and for each pixel p(x,y), calculating a probability $p_l$ of assigning the pixel p(x,y) to the category $C_l$.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
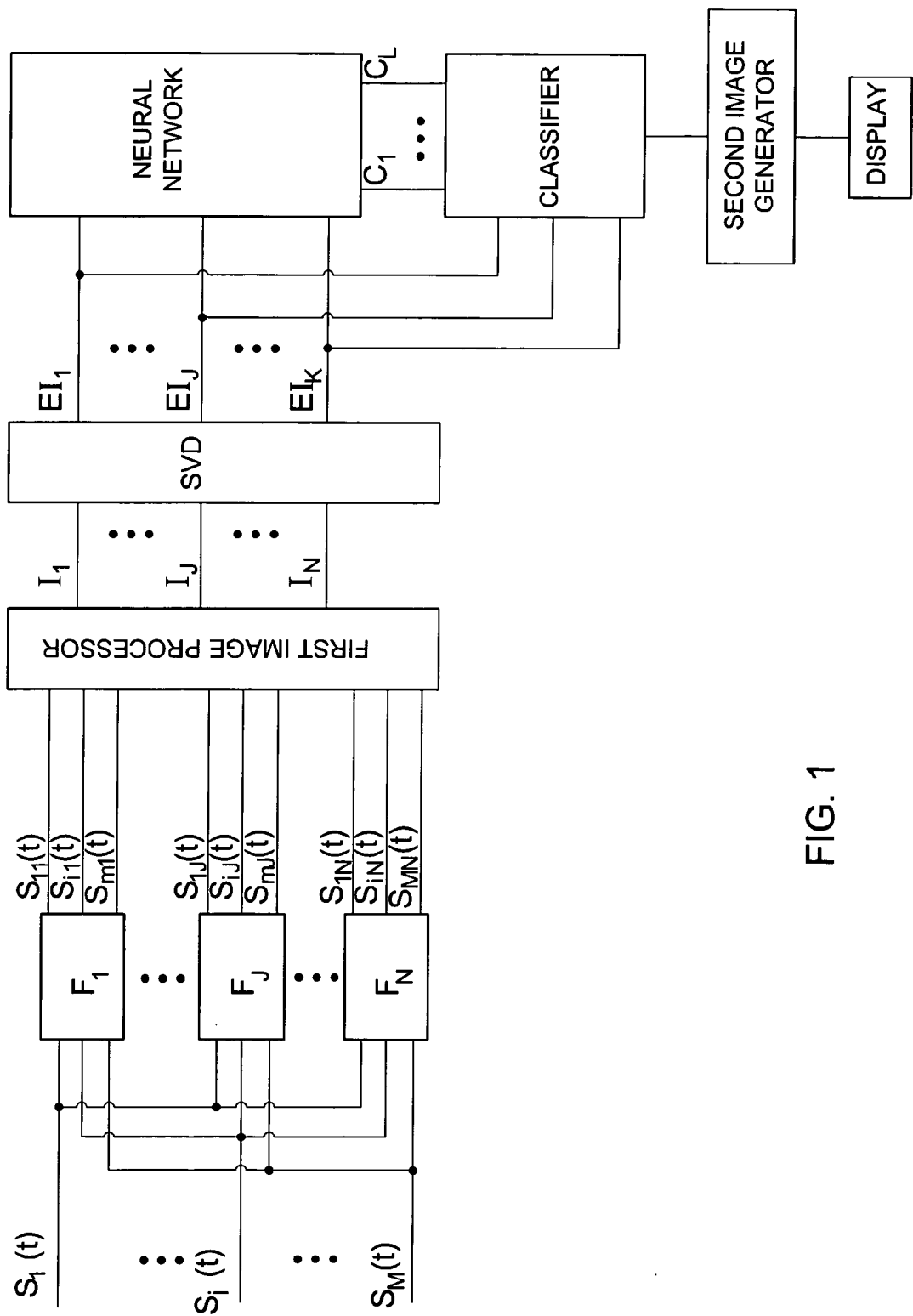
FIG. 1 is a schematic diagram of a system for carrying out the method of the invention, in accordance with one embodiment of the invention.

FIG. 1 shows a schematic diagram of a system for carrying out one embodiment of the method of the invention. M acoustic signals $S_1(t)$ to $S_M(t)$ are obtained during a time interval by placing M microphones on a body surface (not shown) such as an individuals back or chest. The M acoustic signals are each subjected to frequency band filtering by means of N frequency band filters $F_1$ to $F_N$. For each filter $F_j$, j from 1 to N, the M outputs from the filter Fj, Sij(t), i from 1 to M, are input to a first image processor. The first image processor generates N images Ij, j from 1 to N, where each image Ij is obtained using the M outputs of the filter $F_j$. The images $I_j$ may be obtained by any method for generating an image from acoustic signals. For example, the images maybe obtained by the method of Kompis et al. (supra). In a preferred embodiment of the invention, an image is generated by the method disclosed in applicant's WO 03/057037. In the method of WO 03/057037, an image is obtained from M signals P(xi,t) for i=1 to M, (where the signal P(xi, t) is indicative of pressure waves at the location $x_i$; on the body surface) by determining an average acoustic energy $\bar{P}(x,t_1,t_2)$ at at least one position x over a time interval from a first time $t_1$ to a second time $t_2$.

The N images $I_j$, j from 1 to N, are preferably, but not necessarily, transformed by an SVD (singular value decomposition) processor. The SVD processor calculates N eigen-images $EI_j$ and N corresponding eigen-values $\square\lambda_j$, for j from 1 to N, (not shown) where the N eivgen-values $\lambda_j$ are ordered so that $\lambda_1 \leq \lambda_2 \ldots \leq \ldots \leq \lambda_j \leq \ldots \lambda_N$. The SVD processor then determines an integer $K \leq N$ where K is the smallest integer for which $$\frac{\sum_{j=1}^{K} \lambda_j}{\sum_{j=1}^{N} \lambda_j} \leq a,$$

where $\alpha$ is a predetermined threshold. The output of the SVD processor is the K eigen-images $EI_1$ To $EI_K$. The output of the SVD processor is input to a self-organizing map neural network and to a classifier. The output of the neural network consists of L N-dimensional vectors $C_1, \ldots C_L$, where L is a predetermined number of categories of interest. The output from the neural network is input to the classifier. The classifier thus receives as input the K eigen-images $EI_1$ to $EI_K$ from the SVD (or the N images $I_1$ to $I_N$, if a SVD processor is not used) and the L vectors $C_1, \ldots C_L$ from the neural network.

For each pixel p(x,y), the classifier is configured to calculate a probability $p_j$ of assigning the pixel p(x,y) to the category $C_j$. One or more images may then be generated by a second image processor based upon the output from the classifier. For example, for each category Cj, an image may be generated in which the pixel (x,y) has a gray level proportional to the probability that the pixel belongs to the category j. As another example, each category may be assigned a different color, and an image is generated in which each pixel is colored with the color of the category having a maximum probability for that pixel. As yet another example of an image, an image may be generated by selecting, say three categories, and displaying the image on an RGB (red green blue) color display screen. In this example, for each pixel, the red, green, and blue intensity is proportional to the probability that the pixel belongs to the first, second, or third category, respectively. The generated image may be used by a practitioner to identify different tissue types in the image. Generated images may be used to form a data base for automatic learning by the practitioner or by the neural network to analyze the images and identify tissue types in the images.

EXAMPLES

Example 1

Cardiac Imaging 40 acoustic signals $S_i(t)$ arising from an individual's heart were obtained during 0.04 seconds by placing 40 microphones on the individual's back in the cardiac region. The 40 acoustic signals were each subjected to frequency band filtering by means of 3 frequency band filters. For each filter, the 40 outputs from the filter were processed into an image as disclosed in applicant's U.S. Provisional Patent Application No. 60/474,595. The 3 images were input to a self-organizing map neural network The output of the neural network consisted of 5 3-dimensional vectors $C_1, \ldots C_5$, where 5 was the predetermined number of categories of interest. The output from the neural network was input to a classifier.

Figure 2:
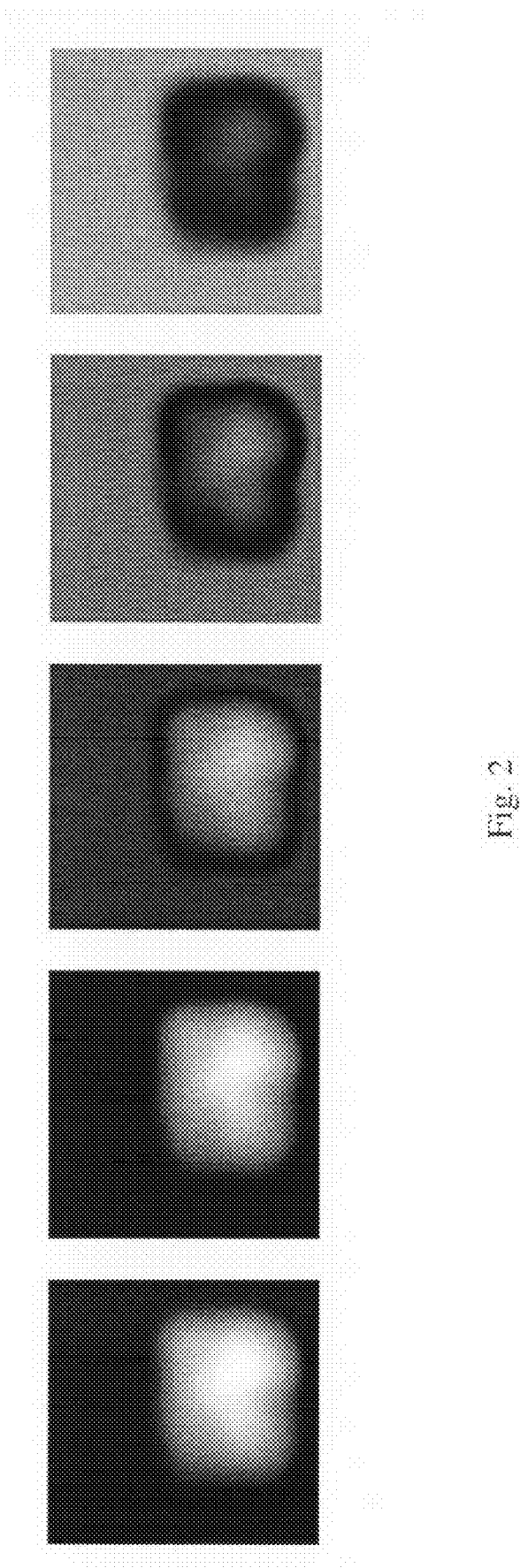
FIG. 2 is shows 5 images of a heart obtained in accordance with one embodiment of the invention.

For each pixel, the classifier calculated a probability $p_i$ of assigning the pixel to the category $P_j$, for j from 1 to 5. An image was then generated for each of three categories in which the pixel $(X_i,y_i)$ has a gray level proportional to the probability that the pixel belongs to that category. The 5 images are shown in FIG. 2.

Example 2

Pulmonary Imaging 40 acoustic signals $S_i(t)$ arising from an individual's lungs were obtained during 0.1 second by placing 40 microphones on the individual's back over the lungs. The 40 acoustic signals were each subjected to frequency band filtering by means of 3 frequency band filters. For each filter, the 40 outputs from the filter were processed into an image as disclosed in applicant's U.S patent application Ser. No. 10/338, 742 having the publication number 2003 01 3967. The 3 images were input to a self-organizing map neural network The output of the neural network consisted of 3 3-dimensional vectors $C_1, \ldots C_3$, where 3 was the predetermined number of categories of interest. The output from the neural network was input to the classifier.

Figure 3A:
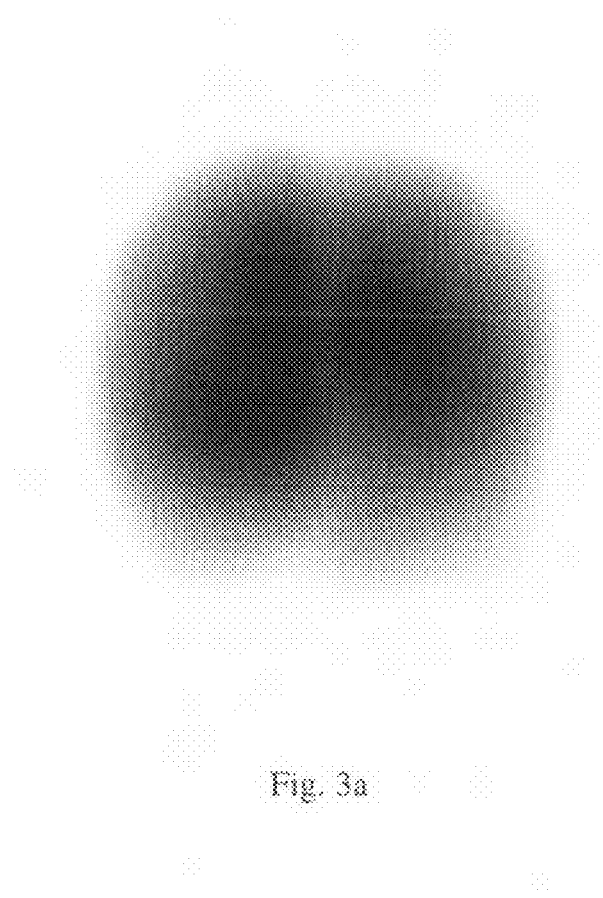
FIG. 3 shows an image of an individual's lungs obtained in accordance with one embodiment of the invention (FIG. 3a) and an image of the same lungs obtained without band pass filtering (FIG. 3b).
Figure 3B:
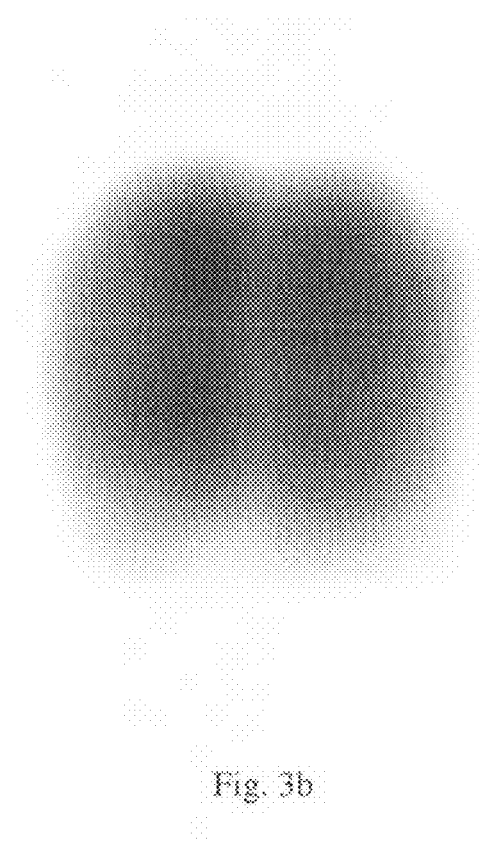

For each pixel, the classifier calculated a probability $p_j$ of assigning the pixel to the category $C_j$, for j from 1 to 3. A color image was then generated as follows. A different color (red green and blue) was used to indicate each of the three categories. In the color image, each pixel p(x,y) has a red, green, and blue level that is proportional to the probability that the pixel belongs to the first, second and third category respectively. A black and white rendition of the color image is shown in FIG. 3a. FIG. 3b shows an image of the individual's lungs obtained from the original sound signals (without frequency filtering) as disclosed in applicant's U.S. patent application Ser. No. 10/338,742 having the publication number 2003 01 3967.

The invention claimed is:

1. A method for tissue differentiation, comprising:
   (a) using M sound transducers to obtain M acoustic signals $s_i(t)$, i=1 to M, from M locations on a body surface;
   (b) for each of N frequency bands, and for each of the signals $s_i(t)$, i from 1 to M, subjecting the signal $s_i(t)$ to band pass filtering using N band-pass filters, so as to generate NXM signals $s_{ij}(t)$, i=1 to M, j=1 to N, wherein N is an integer that is at least 2;
   (c) generating K images $I_1$ to $I_k$; where $K \leq N$, using the signals $S_{ij}(t)$, i=1 to M, j=1 to N, wherein K is an integer that is at least 2;
   (d) dividing pixels into a predetermined number L of categories $C_l$, l from 1 to L, using the images $I_1$ to $I_k$, wherein each category corresponds to a different tissue type; and
   (e) for each category $C_l$, l from 1 to L, and for each pixel p(x,y), calculating a probability $p_l$ of assigning the pixel p(x,y) to the category $C_l$.

2. The method according to claim 1, comprising:
   (a) generating N images $I'_1$ to $I'_N$, wherein the image $I'_j$ is obtained using the signals $s_{ij}(t)$, I from 1 to M, and (b) generating K eigenimages and K eigenvalues using at least two of the N images $I'_1$ to $I'_N$.

3. The method according to claim 1 or 2, wherein the acoustic signals are indicative of cardiac sounds or respiratory tract sounds.

4. The method according to claim 1 wherein the body surface is a chest or a back.

5. The method according to claim 1 wherein an image is obtained from M signals $P(x_i,t)$ for i=1 to M, the signal $P(x_i,t)$ being indicative of pressure waves at the location $x_i$; on the body surface by determining an average acoustic energy $P(x,t_1,t_2)$ at least one position x over a time interval from a first time $t_1$ to a second time $t_2$, using the signals $P(x_i,t)$ for i=1 to M.

6. The method according to claim 1 further comprising generating one or more images using the probabilities $p_l$.

7. A system for tissue differentiation comprising:
(a) M sound transducers configured to obtain M acoustic signals $s_i(t)$, i=1 to M, from M locations on a body surface;
(b) N band pass filters, each band pass filter being configured to receive each of the signals $s_i(t)$, i from 1 to M, so as to generate NXM signals sij(t), i=1 to M, j=1 to N, wherein N is an integer that is at least 2; (c) a first image generator configured to generate K images $I_1$ to $I_K$, where K≦N, using the signals sij(t), i=1 to M, j=1 to N, wherein K is an integer that is at least 2;
(d) a neural network configured to divide pixels into a predetermined number L of categories $C_l$, l from 1 to L, using the images $I_1$ to $I_K$, wherein each category corresponds to a different tissue type; and
(e) a classifier configured, for each category $C_l$, l from 1 to L, and for each pixel p(x,y), calculating a probability $p_l$ of assigning the pixel p(x,y) to the category $C_l$.

8. The system according to claim 7 further comprising a single value decomposition processor, configured to:
(a) receive N images $I'_1$ to $I'_N$, generated by the first image generator, wherein the image $I'_j$ is obtained using the signals $s_{ij}(t)$, I from 1 to M, and
(b) generate K eigenimages and K eigenvalues using the N images $I'_1$ to $I'_N$.

9. The system according to claim 7 wherein the body surface is a chest or a back.

10. The system according to claim 7 wherein the acoustic signals are indicative of cardiac sounds or respiratory tract sounds.

11. The system according to claim 7, wherein the first image generator is configured to generate an image from M signals $P(x_i,t)$ for i=1 to M, the signal $P(x_i,t)$ being indicative of pressure waves at the location $x_i$; on the body surface by determining an average acoustic energy $P(x,t_1,t_2)$ at least one position x over a time interval from a first time $t_1$ to a second time $t_2$, using the signals $P(x_i,t)$ for i=1 to M.

12. The system according to claim 7 further comprising a second image generator configured to generate one or more images using the probabilities $p_l$.

* * * * *